United States Patent [19]

Lindsay

[11] 4,059,700
[45] Nov. 22, 1977

[54] DERMAL TOXICITY OF SOLID COMPOSITIONS CONTAINING A MONTMORILLONITE TYPE OF CLAY AND AN ORGANOPHOSPHORUS PESTICIDE

[75] Inventor: Alexander David Lindsay, East Brunswick, N.J.

[73] Assignee: American Cyanamid Company, Stamford, Conn.

[21] Appl. No.: 658,152

[22] Filed: Feb. 17, 1976

[51] Int. Cl.$^2$ .................................................. A01N 9/36
[52] U.S. Cl. ..................................... 424/216; 424/357
[58] Field of Search ................................ 424/216, 357

[56] References Cited

U.S. PATENT DOCUMENTS

| | | | |
|---|---|---|---|
| 2,596,076 | 5/1952 | Hook et al. | 424/216 X |
| 2,895,873 | 7/1959 | Sawyer, Jr. et al. | 424/357 |
| 3,062,637 | 11/1962 | Marples et al. | 71/2.4 |

Primary Examiner—Allen J. Robinson
Attorney, Agent, or Firm—Harry H. Kline

[57] ABSTRACT

There is provided a composition comprising (a) a major amount of a calcined granular carrier of montmorillonite type of clays and (b) a minor amount of a broad spectrum insecticide-nematocide, namely, 0,0-diethyl S-[(1,1-dimethylethyl)thio]phosphorodithiorate, wherein said composition is distinguished by decreased mammalian dermal toxicity in contrast to conventional solid compositions containing the above-identified insecticide-nematocide.

3 Claims, No Drawings

DERMAL TOXICITY OF SOLID COMPOSITIONS CONTAINING A MONTMORILLONITE TYPE OF CLAY AND AN ORGANOPHOSPHORUS PESTICIDE

The pesticidal component of the composition of the present invention, O,O-diethyl-S-[(1,1-dimethylethyl)-thio]phosphorodithioate, is represented by the formula:

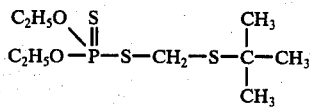

which has been disclosed in U.S. Pat. No. 2,596,076, issued on May 6, 1952, to E. O. Hook as a pesticidal agent. It is known that the latter is highly effective for the control of a broad spectrum of insects and nematodes which attack and destroy agriculturally important food and fodder crops. Thus, it is of advantage to utilize O,O-diethyl S-[(1,1-dimethylethyl)thio]phosphorodithioate in various compositions useful in agriculture. Unfortunately, this otherwise highly effective insecticide-nematocide is extremely toxic to mammals when introduced into the mammalian circulatory system. Although this toxicant may be introduced into the mammalian circulatory system via ingestion and/or inhalation, nonetheless the most commonly encountered mode of entry by far is through dermal absorption.

The use of compositions containing O,O-diethyl S-[(1,1-dimethylethyl)thio]phosphorodithioate for the control of insect and nematode pests of food and fodder crops, therefore, represents a distinct hazard to the individuals engaged in the use and application thereof. Similar hazards are encountered by those who are engaged in storing, transporting and distributing to the ultimate user the above referred-to pesticidal compositions.

It is, therefore, a principal object of the invention to provide a composition containing the above-identified pesticide which will have a low mammalian dermal toxicity while fully retaining its effectiveness for the control of agricultural pests. It is a further object to provide a composition which would offer a margin of safety otherwise not found in conventional compositions containing the aforementioned pesticide. Other objects and advantages will become apparent from a reading of the ensuing description.

Surprisingly, we have found that certain granular compositions comprising a calcined montmorillonite type of clay carrier and a small amount of the above-identified pesticide have advantageously a two to three fold margin of safety due to their lowered mammalian dermal toxicity as compared to similar granular compositions prepared from the above pesticide and a clay carrier other than a montmorillonite type. More particularly, the montmorillonite type clays can be further described as having a crystal lattice of two silica (i.e. aluminum-magnesium silicate) sheets condensed with one gibbsite (i.e. crystalline monoclinic $Al_2O_3 \cdot H_2O$) sheet to form a layer unit. The layer units are stacked one upon the other to form individual particles. Since the large amount of isomorphic substitutions found in these clays makes it impossible to give a theoretical chemical analysis, the following range of components is given as being representative of the montmorillonite type of clays employed in the novel composition of the present invention:

| Component | % by Weight |
| --- | --- |
| Silica ($SiO_2$) | 68–72.5 |
| Iron oxide ($Fe_2O_3$) | 5–7 |
| Aluminum oxide ($Al_2O_3$) | 11–15 |
| Calcium oxide (CaO) | 0.02–1.5 |
| Magnesium oxide (MgO) | 0.8–1.6 |
| Sodium oxide ($Na_2O$) | 0.08–0.4 |
| Potassium oxide ($K_2O$) | 1.1–1.6 |
| Cr, Cu, Mn, Ni | trace |
| Ignition loss | 3–7.5 |

These clays next are calcined at a temperature ranging from about 600° to about 1300° F.

The novel composition of the present invention comprises as a major component from about 95% to 80% (by weight) and, preferably from 90% to 85% (by weight), of a calcined, granular montmorillonite type of clay of about 99% −10 mesh to +70 mesh and, preferably of about 95% −24 mesh to +48 mesh, of the clay as defined above and, as a minor amount, from about 5% to 20% (by weight) and, preferably from 10% to 15% (by weight), of the hereinabove defined pesticide. If desired, a glycol type of clay deactivator can be incorporated into said compositions in amounts ranging from about 1% to 10%, by weight. In this event, the amount of clay carrier is decreased by an amount equal to the deactivator incorporated into said compositions.

In general, the granular compositions are prepared by tumbling and/or cascading the clay granules in a suitable container and spraying the free-flowing granules with a predetermined amount of O,O-diethyl S-[(1,1-dimethylethyl) thio]phosphorodithioate, or an inert solution thereof, said suitable inert solvent being for instance, methylene chloride. Resultant mixture is next agitated until uniform distribution is achieved, and if a solvent is used, drying said granular composition prior to use. The above referred-to deactivator may be added simultaneously with the toxicant.

The compositions of the present invention may be applied to crops or soil by commercially available equipment designed to distribute solid pesticidal compositions.

The present invention is further illustrated by the non-limiting examples set forth below.

EXAMPLE 1

The general procedures for the preparation of granular pesticidal compositions comprising a montmorillonite type of clay and pesticide, namely, O,O-diethyl S-[(1,1-dimethylethyl)thio]phosphorodithioate, are presented as follows:

Method A

The desired quantity of clay granules is charged into a suitable pill coater apparatus modified by the addition of aluminum blades to facilitate the mixing and the flow of clay particles through the spray stream. The required amount of toxicant (and deactivator, if desired) is placed in a stainless steel sprayer adapted so that a nozzle, screen and tip can be used. The container is pressurized to 1.75 kg/cm². The pill coater is started and the toxicant spray stream directed down and into the flowing granules. The sprayer is shaken at intervals to insure a homogeneous spray solution. After the contents have been sprayed, the container is rinsed with a small amount of methylene chloride and spray rinsed onto the granules, and the granules dried by evaporating the methylene chloride.

Method B

The desired quantity of clay granules is charged into a hexagonal polyethylene bowl attached to a variable speed laboratory mixer. The speed of the mixer is adjusted so that the granules cascade down the side of the bowl. The toxicant and deactivator are placed in a 40 ml capacity DeVilbis bottle. A DeVilbis nozzle is attached to the bottle, the air pressure is adjusted to 0.14 to 0.21 kg/cm$^2$ and the contents sprayed onto the cascading granules. After the contents have been sprayed, the container is rinsed with a small amount of methylene chloride and spray rinsed onto the granules, and the granules dried by evaporating the methylene chloride.

The following granular compositions, containing 15%, by weight, of O,O-diethyl S-[(1,1-dimethylethyl)-thio]phosphorodithioate are prepared:

A. Employing Method A and 85%, by weight, of montmorillonite clay, having the following analysis:

| Mineral Component | % by Weight |
|---|---|
| Silica (SiO$_2$) | 72.38 |
| Iron oxide (Fe$_2$O$_3$) | 6.86 |
| Aluminum oxide (Al$_2$O$_3$) | 14.92 |
| Calcium oxide (CaO) | 0.02 |
| Magnesium oxide (MgO) | 1.24 |
| Sodium oxide (Na$_2$O) | 0.08 |
| Potassium oxide (K$_2$O) | 1.52 |
| Ignition loss | 2.98 |

B. Employing Method B and 85%, by weight, of montmorillonite clay, having the analysis given above.

C. Using 85% montmorillonite clay, - Agsorb Oil - dry. Typical analysis:

| Mineral Component | % by Weight |
|---|---|
| Silica (SiO$_2$) | 68.96 |
| Iron oxide (Fe$_2$O$_3$) | 6.28 |
| Aluminum oxide (Al$_2$O$_3$) | 11.67 |
| Calcium oxide (CaO) | 1.47 |
| Magnesium oxide (MgO) | 1.53 |
| Sodium oxide (Na$_2$O) | 0.36 |
| Potassium oxide (K$_2$O) | 1.14 |
| Ignition loss | 7.58 |

D. Using 85% of a non-montmorillonite clay having as a typical analysis the following analysis:

| Mineral Component | % by Weight |
|---|---|
| Silica (SiO$_2$) | 80.4 |
| Iron oxide (Fe$_2$O$_3$) | 0.88 |
| Aluminum oxide (Al$_2$O$_3$) | 9.48 |
| Calcium oxide (CaO) | 0.20 |
| Magnesium oxide (MgO) | 0.54 |
| Sodium and Potassium oxides | 0.15 |
| Ignition loss | 8.35 |

E. Employing a non-montmorillonite clay having the following:

Typical analysis:

| Mineral Component | % by Weight |
|---|---|
| Silica (SiO$_2$) | 59.2 |
| Iron oxide (Fe$_2$O$_3$) | 3.6 |
| Aluminum oxide (Al$_2$O$_3$) | 10.5 |
| Calcium oxide (CaO) | 1.4 |
| Magnesium oxide (MgO) | 10.6 |
| Sodium oxide (Na$_2$O) | 0.11 |
| Potassium oxide (K$_2$O) | 1.0 |
| Ignition loss | 11.4 |

F. Employing a non-montmorillonite clay, 85%, by weight, and having the following analysis:

| Mineral Component | % by Weight |
|---|---|
| Silica (SiO$_2$) | 67.0 |
| Iron oxide (Fe$_2$O$_3$) | 4.0 |
| Aluminum oxide (Al$_2$O$_3$) | 12.5 |
| Calcium oxide (CaO) | 2.5 |
| Magnesium oxide (MgO) | 11.0 |
| Ignition loss | Not Known |

EXAMPLE 2

Dermal toxicity of granular compositions of the present invention as compared to conventional granular compositions containing the same pesticide, using male albino rabbits as test animal.

Materials

1. Five male albino rabbits weighing approximately 2.2 to 3.5 kilograms are selected for each dosage level. The hair is shaved from the entire trunk.
2. Saran tubing or "Vinylite" film, VU 1900, 12 inches wide, 0.04 millimeters thick and of suitable length to fit around the rabbit.
3. One felt cloth bandage measuring approximately 9×18 inches.
4. Four pieces of 1½ inches adhesive tape approximately 14 inches long.

Procedure for Solid Materials

1. The granular composition to be tested is placed in the center of the plastic film and is moistened with water.
2. The rabbits underside is moistened with water and the animals placed belly down on the material. The plastic film is then bought up and around the animal and secured at each end with strips of adhesive tape.
3. The felt cloth is then placed under the belly and brought up and around the animal and secured to the body with the remaining two strips of adhesive tape.

Procedure for Liquid Materials

1. The animal is placed on the plastic film and is wrapped and the film secured with adhesive tape.
2. The test material is then injected under the plastic with an appropriate size needle and syringe.
3. The felt cloth is then placed under the belly and brought up around the animal and secured with the two remaining strips of adhesive tape.

Evaluation

Twenty-four hours after dosing, the "cuff" is removed and any remaining material is brushed away. If the material cannot be removed the animal is fitted with a fiber collar which prevents the animal from licking the treatment area. The animals are observed for 14 days, post dosing, noting signs of toxicity, skin irritation and mortality. At the end of the 14 days the animals are sacrificed and weighted.

By the above procedure the dermal toxicity of the granular compositions prepared in Example 1 is determined. Mammalian dermal toxicity of granular compositions of the present invention as compared to conventional granular compositions containing the same toxicant, using male albino rabbits as test animal. The data obtained are summarized in Table I below:

Table I

| Composition of Example 1 | |
|---|---|
| Toxicant: O,O-diethyl S-[(1,1-dimethylethyl)thio]-phosphorodithioate | LD$_{50}$ in mg/kg Body Weight |
| | 1.0-1.4 |
| A | 37 |
| B | <20 |
| C | 33 |
| D | <10 |
| E | >10 |
| F | <20 |

It can be seen from Table I that the granular compositions of the present invention (A, B, and C) are 2 to 3 times less toxic than the corresponding conventional compositions (D, E, and F).

EXAMPLE 3

Utilizing the procedure of Example 2, the dermal toxicity of the compositions of Example 1 as a function of age (using male albino rabbits as test animal) is determined. The data obtained are summarized in Table II below:

Table II

| Composition of Example 1 | Product Age | LD$_{50}$ in mg/kg Body Weight |
|---|---|---|
| A | One Day | 37 |
| | One Month | 28 |
| | Three Months | 33 |
| | Six Months | 37, 43 |
| | Nine Months | 25, 33 |
| B | One Day | 21 |
| | One Month | >20 |
| | Two Months | 25 |
| | Three Months | >20 |
| | Six Months | 21 |
| | Nine Months | 43 |
| C | One Day | 33 |
| | One Month | 25 |
| | Three Months | 21 |
| | Six Months | 33 |
| | Nine Months | 25 |
| D | One Day | <10 |
| | One Month | >10 |
| | Three Months | <10 |
| | Nine Months | 12 |
| E | One Day | >10 |
| | One Month | >10 |
| | Three Months | >10 |
| | Six Months | 14 |
| | Nine Months | 17 |
| F | One Day | <20 |
| | One Month | <20 |
| | Three Months | <20 |
| | Six Months | 11 |

It can be seen from Table II that the toxicity of these compositions does not change significantly on storage and that the compositions of the present invention are approximately 2 to 3 times less toxic than the corresponding conventional compositions.

EXAMPLE 4

In this example the dermal toxicity of granular compositions of the present invention is evaluated as a function of the calcining temperature of the montmorillonite clay used as carrier. The clay in this example has the following typical analysis:

| Mineral Component | % by Weight |
|---|---|
| Silica (SiO$_2$) | 69.90 |

-continued

| | |
|---|---|
| Iron oxide (Fe$_2$O$_3$) | 5.40 |
| Aluminum oxide (Al$_2$O$_3$) | 14.50 |
| Calcium oxide (CaO) | 0.93 |
| Magnesium oxide (MgO) | 0.86 |
| Cr, Cu, Mn, Na, Ni | trace |
| Ignition loss | 4.30 | and is calcined at three different temperatures:

| Sample | Calcination Temperature |
|---|---|
| 1 | 500-700° F |
| 2 | 800-1000° F |
| 3 | 1200-1300° F |

Accordingly, three compositions are prepared by the methods of Example 1 utilizing the above 3 clay samples.

Each composition comprises 15% by weight of O,O-diethyl S-[(1,1-dimethylethyl)thio]phosphorodithioate (16%, by weight, as is), 4% by weight of a mixture of di- and triethylene glycols and 80% by weight of granular clay carrier.

The dermal toxicity of the compositions is determined by the procedure of Example 2. Dermal toxicity of compositions of the present invention as a function of the calcining temperature of the montmorillonite clay carrier, using male albino rabbits as test animal. The data obtained are summarized in Table III.

Table III

| Sample | Calcining Temperature | LD$_{50}$ in mg/kg Body Weight |
|---|---|---|
| 1. | 500-700° F | 28.3 |
| 2. | 800-1000° F | 37.3 |
| 3. | 1200-1300° F | 49.2 |

It can be seen from Table III that increasing the temperature of calcination of said clay decreases the mammalian toxicity of the compositions prepared therefrom.

We claim:

1. A composition possessing good insecticidal or nematocidal activity and low mammalian toxicity comprising (a) from 80% to 95%, by weight, of a montmorillonite type of clay consisting of 2:1 type of crystal lattice and containing 68% to 72.5%, by weight, of silica (SiO$_2$), 5% to 7%, by weight, of iron oxide (Fe$_2$O$_3$), 11% to 15%, by weight, of aluminum oxide (Al$_2$O$_3$), said clay being calcined at a temperature range from about 600° to about 1300° F, and (b) from 20% to 5%, by weight, of O,O-diethyl S-[(1,1-dimethylethyl)thio]phosphorodithioate.

2. The composition according to claim 1, wherein the 2:1 type of crystal lattice of the montmorillonite type of clay consists of two silica sheets condensed with one gibbsite sheet to form a layer unit and the layer units are stacked one upon the other to form individual particles and wherein said montmorillonite type of clay has the following analysis:

| Mineral Component | % By Weight Range |
|---|---|
| Silica (SiO$_2$) | 68-72.5 |
| Iron oxide (Fe$_2$O$_3$) | 5-7 |
| Aluminum oxide (Al$_2$O$_3$) | 11-15 |
| Calcium oxide (CaO) | 0.02-1.5 |
| Magnesium oxide (MgO) | 0.8-1.6 |
| Sodium oxide (Na$_2$O) | 0.08-0.4 |
| Potassium oxide (K$_2$O) | 1.1-1.6 |
| Cr, Cu, Mn, Ni | trace |
| Ignition loss | 3-7.5 |

3. The composition according to claim 1, comprising 85% to 90%, by weight, of a montmorillonite type clay and the balance being said insecticide or nematocide.

* * * * *